(12) United States Patent
Gagel

(10) Patent No.: US 9,295,770 B2
(45) Date of Patent: Mar. 29, 2016

(54) METHOD FOR DETERMINING A VOLUME FLOW IN A BLOOD TREATMENT APPARATUS, CALCULATING DEVICE AND BLOOD TREATMENT APPARATUS

(75) Inventor: Alfred Gagel, Litzendorf (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 685 days.

(21) Appl. No.: 13/479,850

(22) Filed: May 24, 2012

(65) Prior Publication Data

US 2012/0297869 A1 Nov. 29, 2012

Related U.S. Application Data

(60) Provisional application No. 61/490,083, filed on May 26, 2011.

(30) Foreign Application Priority Data

May 26, 2011 (DE) .......................... 10 2011 103 261
Jul. 4, 2011 (DE) .......................... 10 2011 051 549

(51) Int. Cl.
*A61M 37/00* (2006.01)
*A61M 1/34* (2006.01)
*A61M 1/16* (2006.01)
*A61M 1/36* (2006.01)

(52) U.S. Cl.
CPC ............. *A61M 1/342* (2013.01); *A61M 1/1647* (2014.02); *A61M 1/341* (2014.02); *A61M 1/34* (2013.01); *A61M 1/3663* (2013.01); *A61M 2205/3334* (2013.01)

(58) Field of Classification Search
CPC . A61M 1/342; A61M 1/3441; A61M 1/3639; A61M 1/1647; A61M 1/341; A61M 1/3663; A61M 2205/3334
USPC .......................... 604/5.01, 6.09; 210/645, 741
See application file for complete search history.

(56) References Cited

U.S. PATENT DOCUMENTS 613,395 A * 11/1898 Perfler et al. ................ 235/60.37
4,735,727 A    4/1988 Heitmeier et al.
5,410,916 A    5/1995 Cook
(Continued)

FOREIGN PATENT DOCUMENTS

DE           3202831 C2     8/1983
DE           19650115 C1    7/1998
(Continued)

*Primary Examiner* — Leslie Deak
(74) *Attorney, Agent, or Firm* — Kenyon & Kenyon LLP

(57) ABSTRACT

The present invention relates to a method for determining at least a first volume flow in a blood treatment apparatus which comprises: a primary circuit for conducting the blood to be treated; a secondary circuit for conducting a fluid that is used for the blood treatment; a blood treatment module provided for exchanging fluids and/or substances between the primary circuit and the secondary circuit; and an optionally provided fluid connection between the primary circuit and the secondary circuit, provided for introducing the first volume flow from the secondary circuit into the primary circuit; wherein the method encompasses determining the first volume flow of the secondary circuit taking into account a first pressure value or pressure measurement and a second pressure value or pressure measurement in the secondary circuit. The present invention further relates to a calculating device and a blood treatment apparatus.

10 Claims, 4 Drawing Sheets

(56) References Cited

U.S. PATENT DOCUMENTS

| | | |
|---|---|---|
| 5,660,722 A | 8/1997 | Nederlof |
| 6,039,877 A | 3/2000 | Chevallet et al. |
| 6,129,702 A | 10/2000 | Woias et al. |
| 6,406,631 B1 * | 6/2002 | Collins et al. ............ 210/646 |
| 2003/0136181 A1 | 7/2003 | Balschat et al. |
| 2009/0234289 A1 | 9/2009 | Gagel et al. |

FOREIGN PATENT DOCUMENTS

| | | |
|---|---|---|
| DE | 69902250 T2 | 12/2002 |
| DE | 10201109 C1 | 1/2003 |
| DE | 69532258 T2 | 9/2004 |
| DE | 102005023430 A1 | 9/2006 |
| EP | 0694312 A2 | 1/1996 |
| EP | 1029554 A2 | 8/2000 |
| EP | 1681068 A1 | 7/2006 |
| FR | 2520621 A | 1/1983 |
| FR | 2777992 A | 10/1999 |
| FR | 2777992 A1 | 10/1999 |
| WO | 2000-023140 A1 | 4/2000 |
| WO | 2008-125894 A1 | 10/2008 |

* cited by examiner

METHOD FOR DETERMINING A VOLUME FLOW IN A BLOOD TREATMENT APPARATUS, CALCULATING DEVICE AND BLOOD TREATMENT APPARATUS

CROSS REFERENCE TO RELATED APPLICATIONS

This application claims the benefit of U.S. Provisional Application No. 61/490,083 filed on May 26, 2011, German Patent Application DE 10 2011 103 261.8, filed May 26, 2011, and German Patent Application DE 10 2011 051 549.6, filed Jul. 4, 2011, each of which is incorporated herein in its entirety by reference.

FIELD OF INVENTION

The present invention relates to a method for determining a volume flow, as well as a calculating device and a blood treatment apparatus. Furthermore, the present invention relates to a digital storage medium, a computer program product, as well as a computer program.

BACKGROUND OF THE INVENTION

In some methods of extracorporeal blood treatment, substituate liquid is supplied to the utilized extracorporeal blood circuit and/or a blood treatment module, e.g., the blood filter. Determining the size of such substituate flow or other volume flows is not reliably possible under practical conditions.

One object of the present invention is an improved method for determining a volume flow in a blood treatment apparatus. Furthermore, a suitable calculating device, a corresponding blood treatment apparatus as well as a digital storage medium, a computer program product and a computer program are specified.

According to the present invention, a method for determining at least a first volume flow in a blood treatment apparatus is proposed. The blood treatment apparatus comprises: a primary circuit for conducting the blood to be treated, a secondary circuit for conducting a fluid that is used for the blood treatment, and a blood treatment module as a section of the primary circuit and/or of the secondary circuit which is provided for exchanging fluids and/or substances between the primary circuit and the secondary circuit. The blood treatment apparatus may optionally comprise a fluid connection between the primary circuit and the secondary circuit, provided for introducing the first volume flow from the secondary circuit into the primary circuit.

The method encompasses determining the first volume flow of the secondary circuit taking into account a first pressure measurement and a second pressure measurement in the secondary circuit. Alternatively or additionally, the method may encompass determining a volume flow of the secondary circuit upstream from the blood treatment module taking into account or considering a first pressure difference, and/or determining a volume flow of the secondary circuit downstream from the blood treatment module taking into account or considering a second pressure difference.

The calculating device according to the present invention is provided and/or programmed for executing the method according to the present invention.

The blood treatment apparatus according to the present invention is provided for extracorporeally treating blood. It is further embodied and provided for executing or performing the method according to the present invention. It comprises at least or is connected herewith: a calculating device according to the present invention, a primary circuit for conducting the blood to be treated, a secondary circuit for conducting a fluid that is used for the blood treatment, a blood treatment module as a section of the primary circuit and/or of the secondary circuit, which is provided for exchanging fluids and/or substances between the primary circuit and the secondary circuit, and a fluid connection between the primary circuit and the secondary circuit, provided for introducing the first volume flow from the secondary circuit into the primary circuit.

All advantages resulting from the method according to the present invention may in certain embodiments according to the present invention undiminishedly also be achieved by use of any of the subjects according to the present invention. In some embodiments according to the present invention, this also applies for the digital storage medium according to the present invention, the computer program product according to the present invention and the computer program according to the present invention.

A digital, particularly a non-volatile storage medium according to the present invention, particularly in the form of a machine-readable data storage device, particularly in the form of a disk, CD, DVD or EPROM, particularly with electronically or optically readable control signals, may interact with a programmable computer system such that the mechanical steps of a method according to the present invention are prompted.

Hereby, all, several or some of the mechanically executed steps of the method according to the present invention may be prompted.

A computer program product according to the present invention comprises a program code stored on a machine-readable data storage device for prompting the mechanical steps of the method according to the present invention when the computer program product runs on a computer. According to the present invention a computer program product can be understood as, for example, a computer program which is stored on a storage device, an embedded system as a comprehensive system with a computer program (e.g. an electronic device with a computer program), a network of computer-implemented computer programs (e.g. a client-server system, a cloud computing system, etc.), or a computer on which a computer product is loaded, executed, saved or developed.

A machine-readable data storage device denotes in certain embodiments of the present invention a medium that contains data or information which is interpretable by software and/or hardware. The medium may be a disk, a CD, DVD, a USB stick, a flash card, an SD card or the like.

A computer program according to the present invention comprises a program code for prompting the mechanical steps of a method according to the present invention when the computer program runs on a computer. A computer program according to the present invention can be understood as, for example, a physical software product, which is ready for distribution and contains a computer program.

It also applies for the computer program product according to the present invention and the computer program according to the present invention that all, several or some of the mechanically executed steps of the method according to the present invention are prompted.

Embodiments according to the present invention may comprise one or more of the features named hereafter. Additionally, embodiments according to the present invention are the subject of the dependent claims.

In all of the following embodiments, the use of the expression "may be" or "may have" and so on, is to be understood synonymously with "preferably is" or "preferably has,"

respectively, and so on, and is intended to illustrate certain embodimentts according to the present invention.

In some embodiments according to the present invention, the primary circuit and/or the secondary circuit is a closed circuit. In other embodiments according to the present invention, the primary circuit and/or the secondary circuit is an open circuit or a non-closed circuit.

In some embodiments according to the present invention, the secondary circuit is a dialysate circuit. In other embodiments according to the present invention, it is not a dialysate circuit.

In certain embodiments according to the present invention, a volume flow is a flow rate.

In some embodiments according to the present invention, the first volume flow is a substituate flow.

In some embodiments according to the present invention, the first volume flow is an ultrafiltration flow.

In some embodiments according to the present invention, "determining" stands for quantitative determining. In other embodiments according to the present invention, "determining" stands for qualitative determining. The latter may, e.g., be or encompass specifying the first volume flow as a proportion of a second volume flow or a total volume flow.

In some embodiments according to the present invention, the first pressure measurement and the second pressure measurement are or will be measured at different measuring points within the secondary circuit.

In some embodiments according to the present invention, the first pressure difference and the second pressure difference relate to pressure differences within the secondary circuit.

In some embodiments according to the present invention, the first measuring point is located upstream from each blood treatment module, e.g., upstream from each dialysis filter, and the second measuring point is located downstream from each blood treatment module, e.g., downstream from each dialysis filter. If the section of the dialysis filter encompasses several dialysis filters that are separate from each other, they may in some embodiments according to the present invention be considered as a joint dialysis filter.

In some embodiments according to the present invention, the pressure sensors do not serve to determine the respective filtrate flow or another flow through the membrane of a blood treatment filter.

In certain embodiments according to the present invention, the first pressure measurement indicates a pressure in the secondary circuit at a first pressure measurement point upstream from the blood treatment module, namely downstream from a split, separation or junction of the first volume flow from a second—preferably larger—volume flow.

In some embodiments according to the present invention, the volume flow is split in a dialyzing liquid filter or an online filter. An online filter may be a filter in which the amount of liquid the dialysis machine needs or allows for substitution, and which is taken from the closed system before the dialyzer, is filtered again.

In some embodiments according to the present invention, the second pressure measurement specifies a pressure in the secondary circuit at a second pressure measurement location, which is located downstream from the blood treatment module.

In some embodiments according to the present invention, the first volume flow branches off a second volume flow and/or is a partial flow of the second volume flow. In certain embodiments according to the present invention, the first volume flow is taken from the second volume flow by use of a pump, e.g., by use of a substituate pump, and conveyed into the primary circuit or into the blood treatment module.

In some embodiments according to the present invention of the method, a flow resistance between the first pressure measurement location and the second pressure measurement location is determined as a function of the second volume flow and the difference between second pressure measurement and first pressure measurement.

In some embodiments according to the present invention, the function of the flow resistance is linearized in the area of at least one operating point.

An operating point may be specified by use of a volume flow and a pressure difference. A linearization is given, e.g., when adjacent operating points in a predefined volume flow area/pressure difference area are located on a straight line that may be mathematically described. The correlation of the measuring points with the straight line may be specified by use of the correlation coefficient $R^2$. A sufficiently accurate linearization may, e.g., be predefined by use of a correlation coefficient $R^2$ greater than or equal 0.995.

In some embodiments according to the present invention, the first volume flow is determined as a function of the flow resistance, the second volume flow and the difference between second pressure measurement and first pressure measurement.

In some embodiments according to the present invention, the first volume flow is determined as a function of the flow resistance, the second volume flow and the difference between second pressure measurement and first pressure measurement only then when the first volume flow is small as compared to the second volume flow. The first volume flow is in some embodiments according to the present invention to be regarded as small when it is max. 4% or max. 8% of the second volume flow.

In some embodiments according to the present invention, the functional connection of a pressure loss between first pressure measurement location and a section within the blood treatment module is determined by the factory before the beginning of the blood treatment depending on the second volume flow in the secondary circuit or was determined this way.

In some embodiments according to the present invention, the section within the blood treatment module is its center.

The center of the blood treatment module may relate to the distance of the flow on the side of the primary circuit or secondary circuit.

The first volume flow may hereby be zero or be set to zero.

In some embodiments according to the present invention, the functional connection of a pressure loss between first pressure measurement location and a section within the blood treatment module is determined depending on the second volume flow in the secondary circuit as a function of a pressure loss or it was determined this way. This pressure loss occurs between the first pressure measurement location and the second pressure measurement location and depends on the second volume flow. In this case, the pressure loss due to the flow resistance from the first pressure measurement location to a section within the blood treatment module is extrapolated in order to encompass also the flow resistance which occurs up to the second pressure measurement location. This is normally permissible especially then when both flow sections are equally or similarly structured and therefore comprise equal or similar flow resistances.

In some embodiments according to the present invention, the pressure loss between first pressure measurement location and second pressure measurement location is determined—or was determined at a time before the beginning of the treatment—exclusively or not exclusively, considering the pressure loss between the first pressure measurement location and the second pressure measurement location depending on the second volume flow and the volume flow that transfers in the treatment module from the primary circuit into the secondary circuit as UF rate or transmembrane flow.

The sum of the second volume flow and the volume flow that is transported in the treatment module from the primary circuit into the secondary circuit basically corresponds to the volume flow that flows in the second section, i.e., from the blood treatment module to the second pressure measurement location, provided that the first volume flow is significantly smaller than the second volume flow, e.g., max. 10%. As this volume flow is unrealistically high, however, for determining the flow resistance and thus the pressure loss for the whole distance, i.e., from first to second pressure measurement location, a pressure loss proportion of the first section is deducted. This proportion may be approximately determined by use of the total differential:

$$\left(\frac{dF_{1,m}}{dQ}\right)_{(Q_{BK}+Q_{UF}+Q_d)/2} * Q_{sub}$$

with:
$F_{1,m}$—pressure loss as function of the volume flow between first pressure measurement location and the center of the blood treatment module;
$Q_{BK}$—second volume flow;
$Q_{UF}$—volume flow which transfers in the blood treatment module from the primary circuit into the secondary circuit; and
$Q_d$—second volume flow less the first volume flow.

In some embodiments according to the present invention, a leakage or a leakage rate, which results from or accompanies differently sized volume flows in the secondary circuit downstream and upstream from the blood treatment module, is determined. For determining this, a functional connection of the following parameters is determined or specified, among which are: the first pressure measurement; the second pressure measurement; the flow resistance between first pressure measurement location and a section within the blood treatment module; the flow resistance between the section within the blood treatment module and the second pressure measurement location; the first volume flow; the second volume flow; and—optionally—a third volume flow. The third volume flow corresponds to a fluid exchange or fluid transfer via a membrane between the primary circuit and the secondary circuit of the blood treatment module.

In certain embodiments according to the present invention, a functional connection is understood as a function, a relationship, a mathematical relationship, a formula or the like.

In some embodiments according to the present invention, the tightness of the secondary circuit against an exterior of the secondary circuit is determined between a first valve upstream from the blood treatment module and a second valve downstream from the blood treatment module. These embodiments encompass closing the first valve and closing the second valve. Subsequently, the fluid system upstream from the first valve and/or downstream from the second valve is impinged with an overpressure. This may, e.g., take place by use of the dialysate pump. Hereby, it is checked or monitored whether the overpressure in the fluid system changes within a predefined time span. Additionally or alternatively, it is checked or monitored whether the overpressure changes or decreases. If a pressure drop or pressure decrease beyond a predefined pressure range is detected, the secondary circuit or its section that is tested for tightness is detected as being leaky. The check for pressure drop may take place by use of the first pressure measurement location and/or by use of the second pressure measurement location.

Optionally, it may be checked or ensured in these embodiments whether the first volume flow is zero. Ensuring that the first volume flow is zero takes place in that, e.g., no flow is generated by the substituate pump.

In some embodiments according to the present invention, a leakage in the secondary circuit is found and the blood treatment apparatus or even only an ultrafiltration is stopped for patient safety reasons if the found pressure drop is outside the predefined pressure range.

In some embodiments according to the present invention, an offset error in determining the volume flow is found when the volume flows of the secondary circuit are differently sized downstream and upstream from the blood treatment module, if the pressure drop is not outside the predefined pressure range. This offset may be included in further measurements and/or be considered for the treatment of the patient without having to interrupt the blood treatment.

In some embodiments according to the present invention, a volume flow upstream and/or a volume flow downstream from the blood treatment module is determined by a pressure difference determination at defined flow resistances.

Such defined or known flow resistances may appear at valves, apertures or other components present in the circuit.

In some embodiments according to the present invention, an offset for the volume flow determinations is determined. This encompasses checking, particularly according to an approach as described above, whether the secondary circuit or a viewed section hereof is tight against an external environment and/or a further line section. It further encompasses checking or ensuring whether or that no fluid between the primary circuit and the secondary circuit, for example, via the blood treatment module, is exchanged. Again further, this procedure encompasses determining a difference between the volume flow upstream and the volume flow downstream from the blood treatment module in the secondary circuit. This may be determined, e.g., according to a method as described above.

Finally, this procedure encompasses setting the difference between the volume flows—or a value correlating herewith—as offset.

In certain embodiments according to the present invention, the method encompasses determining a fluid exchange or fluid transfer—or a value therefor—in the blood treatment module between the primary circuit and the secondary circuit. Such fluid exchange is deemed to be determined when differently sized volume flows in the secondary circuit are found downstream and upstream from the blood treatment module.

Such fluid exchange may be equated to the whole transmembrane flow which basically corresponds to the ultrafiltration rate (UF).

If such fluid exchange is found, it may be checked in a subsequent step whether an offset or a leakage is present. The results of this check are included in the further dialysis treatment by either setting an offset or terminating the treatment of the patient.

In some embodiments according to the present invention, determining the first, second, third and/or fourth pressure measurement is part of the method, in others it is not. Determining the pressure values may take place directly, e.g., by direct measurement, or indirectly. It is therefore called a pressure measurement even then when the pressure is not measured but determined or set otherwise, e.g., by calculating from other quantities.

In certain embodiments according to the present invention, the calculating device comprises or is connected with one or more controlling or regulating units for controlling or regulating a blood treatment apparatus.

In some embodiments according to the present invention, the calculating device is suited and configured for qualitatively determining the first volume flow of the secondary circuit as a proportion of a second volume flow.

In some embodiments according to the present invention, the blood treatment apparatus comprises the devices that are necessary and provided or configured for executing the method according to the present invention. This especially applies for the devices mentioned in relation with the method disclosed herein. A blood treatment device can comprise—as any other device according to the present invention—at least one or more devices suited and/or configured and/or adapted such that one, more or all steps mentioned in here can be executed by the respective device.

In certain embodiments according to the present invention, the fluid connection, which is only optional and provided for introducing the first volume flow from the secondary circuit into the primary circuit, is a line, in particular a tube line or connecting line.

In some embodiments according to the present invention, the fluid connection is and/or comprises no filter membrane.

In some embodiments according to the present invention, the blood treatment apparatus comprises at least or exactly two pressure measurement locations located in the secondary circuit upstream from the blood treatment module and/or after branch-off of the fluid connection from the secondary circuit.

Additionally or alternatively, the blood treatment apparatus comprises in these embodiments two pressure measurement locations located in the secondary circuit downstream from the blood treatment module.

In some of the latter embodiments according to the present invention, each of at least two pressure measurement locations, e.g., the first and the third, or the second and the fourth, are located upstream or downstream from a known flow resistance. Thus, the first and the third pressure measurement location may be located or may measure upstream or downstream from the first valve. Further, the second and the fourth pressure measurement location may be located or may measure upstream or downstream from the second valve.

In certain embodiments according to the present invention, the blood treatment apparatus is a hemofiltration apparatus or a hemodiafiltration apparatus.

In some embodiments according to the present invention, the blood treatment module is a blood filter, a dialysis filter or a hemodialysis filter.

Some, a few or certain embodiments according to the present invention comprise one, some or all of the following advantages:

According to the present invention, there is advantageously no need for an apparatus for measuring the substitute flow or the dialyzer flow directly.

Hemodialysis is a method for removing uremic substances and for removing liquid from the blood of patients that suffer from renal insufficiency. During hemodialysis, the patient's blood is purified outside the body in a dialyzer. The dialyzer comprises a blood chamber and a dialyzing liquid chamber which are separated by use of a semi-permeable membrane. During the treatment, the patient's blood flows through the blood chamber. In order to purify the blood effectively from uremic substances, fresh dialyzing liquid continually flows through the dialyzing liquid chamber.

While in hemodialysis (HD) the transport of the smaller molecular substances through the membrane of the dialyzer is basically determined through the differences in concentration (diffusion) between the dialyzing liquid and the blood, in hemofiltration (HF) substances dissolved in plasma water, in particular substances of higher molecular weight, are effectively removed through a high liquid flow (convection) through the membrane of the dialyzer. In hemofiltration, the dialyzer serves as filter. A combination of both methods is the hemodiafiltration (HDF).

During hemo(dia)filtration, a part of the serum that was removed through the membrane of the dialyzer is replaced by a sterile substitution liquid which generally is supplied to the extracorporeal blood circuit either upstream from the dialyzer or downstream from the dialyzer. The supply of the substitution liquid upstream from the dialyzer is also called "predilution," the supply downstream from the dialyzer "postdilution."

The substituate flow may also be determined indirectly. This could be calculated depending on the type of the utilized substituate pump, e.g., indirectly from the rotational speed and the stroke volume of the substituate pump, which may be designed as an occluding tube roller pump, that is dependent on the input pressure. However, the real substituate flow may deviate more or less from the calculated substituate flow due to, e.g., tube kinking or incomplete occlusion of the pump tube and the like. Such errors or deviations between substituate flow that was indirectly determined and actual substituate flow are regularly not to be found through known monitoring methods such as, e.g., TMP monitoring; the accuracy in balancing is not affected with such deviations in TMP monitoring (TMP—transmembrane pressure). The present invention advantageously solves this in some embodiments.

In HDF treatments, the clearance is determined with middle molecules of the substituate flow. Deviations in the substituate flow are thus reflected in the administered dialysis dose of the treatment. The accuracy and the safety of the treatment of the patient may thus advantageously be increased in some embodiments, if the exact substituate flow is known.

An advantage of some embodiments according to the present invention is the accuracy in determining the substituate flow. The achievable accuracy is based, inter alia, on the assumption that the flow resistances $R_1$ and $R_2$ are caused by non-exchangeable hydraulics components of the blood treatment apparatus used for the treatment, which are used for calculating according to the present invention the substituate flow. Thus, the calculation is not based on the flow resistance of disposables that are specifically chosen and used for the individual treatment session (e.g., dialyzers with in part very different ultrafiltration coefficients), the flow differences of which may differ from type to type and even from disposable to disposable of the same type. The achievable accuracy is, inter alia, also based on the assumption that all fluids to be considered with the volume flow determination are fluids the properties of which are known and in addition not changeable. This applies, e.g., for dialysate on which the calculations described herein are based. The same assumption, however, does not also apply for other fluids such as blood. Its viscosity may vary from treatment to treatment due to a changed composition (Hkt, TP, fibrinogen, etc.). Furthermore, viscosity of blood may also change during a treatment due to the water removal. During hemodiafiltration treatments, the effective UF capacity of the dialyzer may additionally change due to the construction of a reversible secondary membrane depending on the substitute rate and the treatment mode (pre-/postdilution). This is advantageously also not an issue in the method according to the present invention.

During the dialysis treatment, the transmembrane flow or the UF rate may constantly be determined by use of the pressure difference measurement and with the previously determined flow resistance measurement. This may also advantageously contribute to increasing patient safety.

BRIEF DESCRIPTION OF THE DRAWINGS

Hereafter, the present invention is exemplarily explained with reference to the appended figures. In the figures, identical reference numerals refer to same or identical components. The arrows always indicate a direction of flow of the respective fluid. It applies that.

DETAILED DESCRIPTION OF THE DRAWINGS

Figure 1:
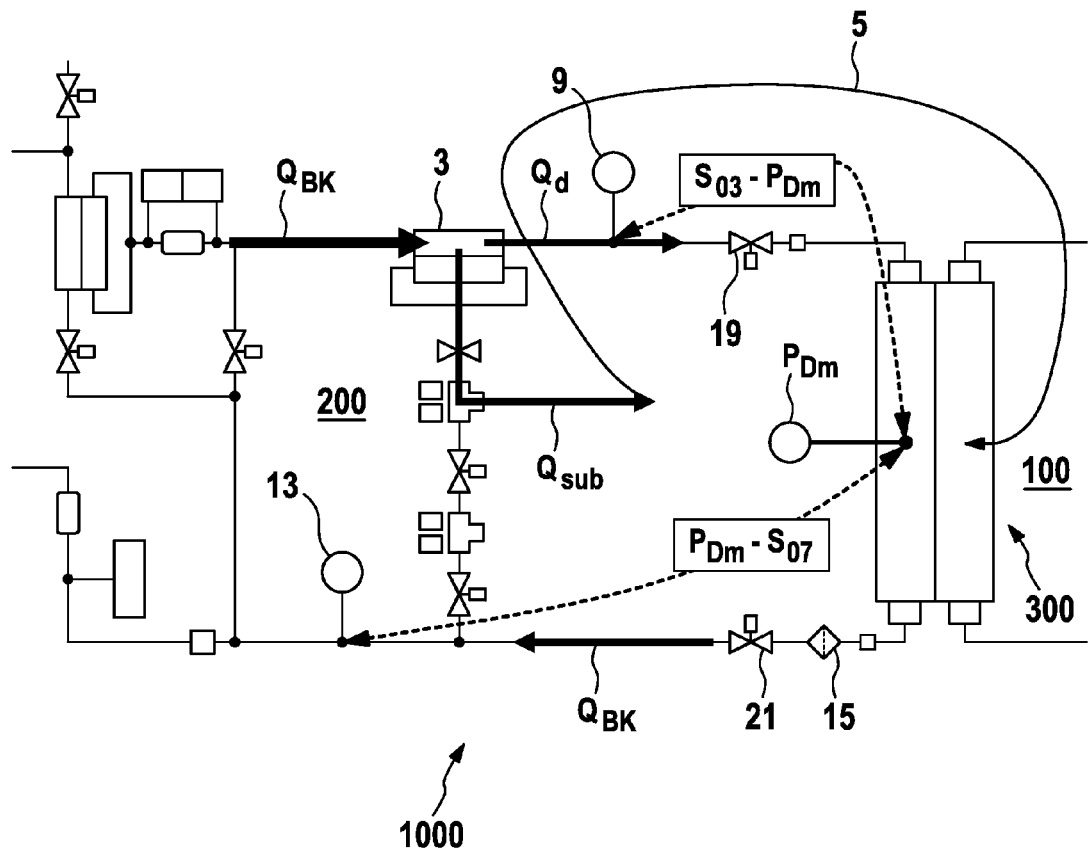
FIG. 1 shows details of a schematically simplified blood treatment apparatus with a primary circuit and a secondary circuit according to a first embodiment of the present invention.

FIG. 1 schematically shows a detail of a hemodiafiltration apparatus (hereafter also shortened to HDF) as an example of a blood treatment apparatus 1000 according to the present invention with a primary circuit 100 and a secondary circuit 200. The primary circuit 100 and the secondary circuit 200 each flow through a joint blood treatment module 300, here exemplarily illustrated as a blood filter or dialyzer.

A first volume flow, hereafter denoted as substituate flow $Q_{sub}$, and a third volume flow, hereafter denoted as dialyzer flow $Q_d$, are created by separating a second volume flow, hereafter denoted as dialysate flow $Q_{BK}$. The separation occurs in a filter 3 of the secondary circuit 200.

The substituate flow $Q_{sub}$ is taken from the dialysate flow $Q_{BK}$, e.g., by use of a substituate pump. The substituate flow $Q_{sub}$ is introduced into the primary circuit 100, an extracorporeal blood circuit, by use of a fluid line or fluid connection 5 which is only indicated by an arrow in FIG. 1.

The dialyzer flow $Q_d$ flows through the blood treatment module 300 in the secondary circuit 200.

These volume distributions and relations may be illustrated by use of the following equation:

$$Q_{BK} = Q_d + Q_{sub} \tag{1}$$

$Q_{BK}$—dialysate flow;
$Q_d$—dialyzer flow;
$Q_{sub}$—substituate flow;

Before the dialysate flow $Q_{BK}$ is split as described above, it flows through a balancing chamber of the secondary circuit 200 in the present example. The balancing chamber allows for determining the dialysate flow $Q_{BK}$ as a function of a calibrated balancing chamber volume and a loading time of the balancing chamber:

$$Q_{BK} = \frac{V_{BK}}{T_{BK}}$$

with:
$Q_{BK}$—dialysate flow;
$V_{BK}$—calibrated balancing chamber volume; and
$T_{BK}$—loading time of the balancing chamber.

In the present embodiment, a faultlessly working apparatus is viewed in which no erroneous balancing occurs. Further, it is assumed that the ultrafiltration rate $Q_{UF}$ (or, UF rate) is negligibly small as compared to the substituate flow $Q_{sub}$.

Downstream from the filter 3, the first pressure measurement $S_{03}$ of the dialyzer flow $Q_d$ is measured by use of a first pressure sensor 9. The pressure value in the center of the blood treatment module 300 is denoted as $P_{Dm}$. Thus, the pressure difference of the dialyzer flow $Q_d$ between the first pressure measurement location 9 and the center of the blood treatment module 300 corresponds to the term $S_{03}-P_{Dm}$.

Between first pressure measurement location 9 and the center of the dialyzer 300 there is a flow resistance $R_1$. The flow resistance $R_1$ is a function of the dialyzer flow $Q_d$:

$$R_1 = f(Q_d)$$

with:
$R_1$—flow resistance between first pressure measurement location 9 and the center of the dialyzer 300; and
$Q_d$—dialyzer flow.

Thus, the pressure difference $S_{03}-P_{Dm}$ results in:

$$S_{03} - P_{Dm} = Q_d * R_1 = (Q_{BK} - Q_{sub}) * R_1 \tag{2}$$

In this embodiment, the substituate flow $Q_{sub}$, which flows into the dialyzer 300, is completely transferred from the primary circuit 100 into the secondary circuit 200 again or transported through the membrane which is located in the dialyzer 300. Therefore, the dialysate flow $Q_{BK}$ escapes again to the side of the secondary circuit 200 at the output of the blood treatment module 300.

Further downstream from the dialyzer 300, a second pressure measurement $S_{07}$ is measured in the secondary circuit 200 at a second pressure sensor 13. Thus, the pressure difference between the center of the blood treatment module 300 and the second pressure sensor 13 results in $P_{Dm}-S_{07}$.

Analogous to $R_1$, a flow resistance $R_2$ is further introduced, it specifies the flow resistance which is present between the center of the dialyzer 300 and the second pressure measurement location 13. It applies that:

$$P_{Dm} - S_{07} = Q_{BK} * R_2 \tag{3}$$

The addition of the equations (2) and (3) results in:

$$S_{03} - S_{07} = Q_d * R_1 Q_{BK} * R_2 = (Q_{BK} - Q_{sub}) * R_1 + Q_{BK} * R_2 \tag{4a}$$

or $$S_{03} - S_{07} = Q_{BK} * (R_1 + R_2) - Q_{sub} * R_1 \tag{4b}$$

From this, the substituate flow $Q_{sub}$ may be calculated:

$$Q_{sub} = Q_{BK} * \left(1 + \frac{R_2}{R_1}\right) - \frac{S_{03} - S_{07}}{R_1} \tag{5}$$

The flow resistances $R_1$ and $R_2$ are exclusively caused by components of the secondary circuit 200. They all contribute to the flow resistance mostly equally in practice, except for a dialysate filter 15 which, however, creates only a small pressure drop. Therefore, the flow resistances $R_1$ and $R_2$ are assumed to be commensurate in first approximation. With the simplification $R_1=R_2=R$, the following is obtained:

$$S_{03}-S_{07}=R*(2*Q_{BK}-Q_{sub}) \tag{6}$$

Figure 2:
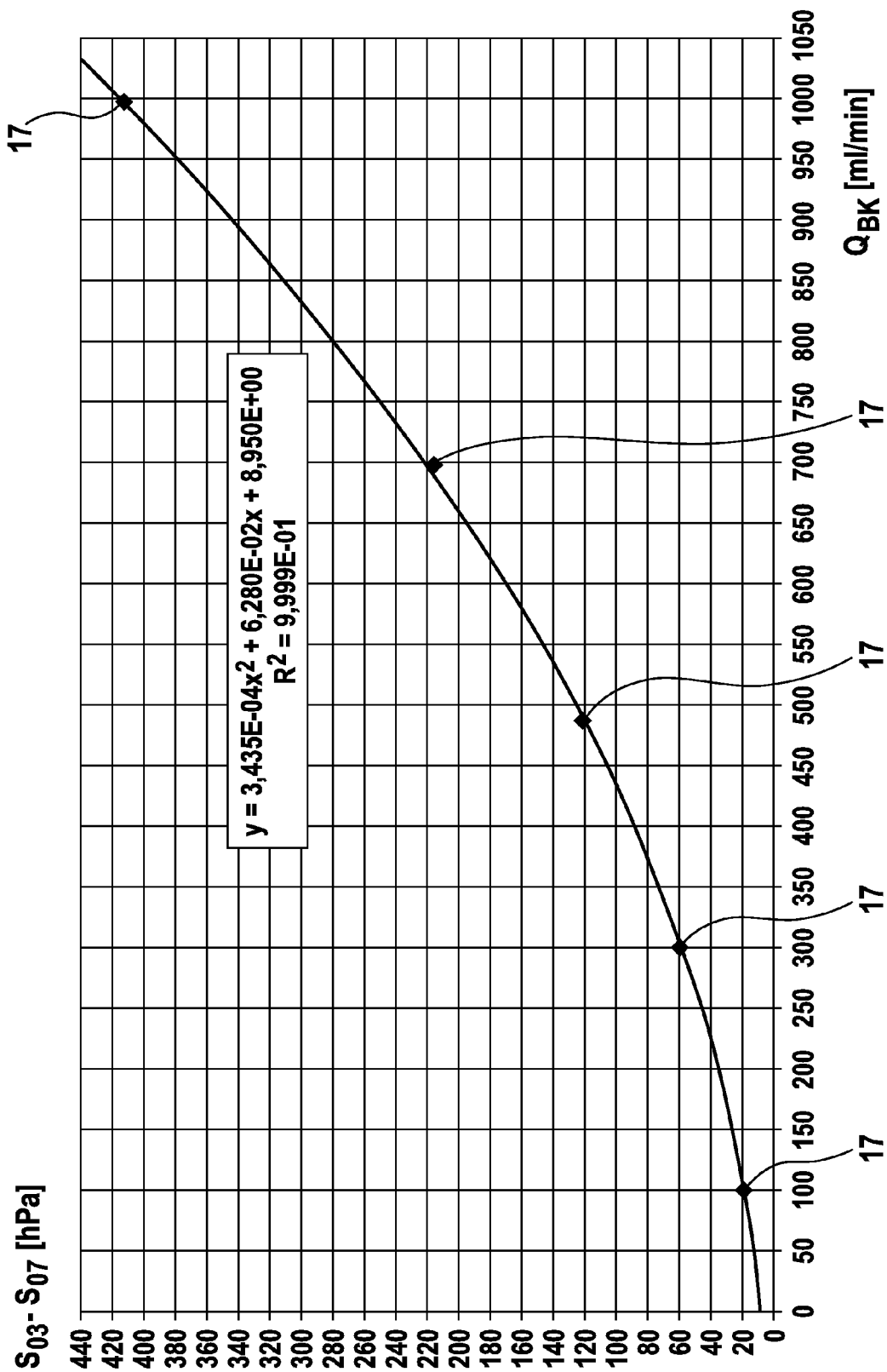
FIG. 2 shows a measured curve of a pressure difference in the secondary circuit between a first and a second pressure measurement location over a second volume flow for determining a flow resistance.

FIG. 2 shows a measured curve of the pressure difference between the first pressure measurement $S_{03}$ measured at the first pressure measurement location 9 and the second pressure measurement $S_{07}$ measured at the second pressure measurement location 13 over the dialysate flow $Q_{BK}$ in the secondary circuit 200. The substitute flow $Q_{sub}$ is zero ($Q_{sub}=0$ ml/min). The blood flow in the primary circuit is $Q_b=450$ ml/min.

In FIG. 2, five measuring points 17 are marked. The measuring points were recorded between the pressure difference values 20 hPa to 420 hPa and with dialysate flows $Q_{BK}$ between 100 ml/min and 1,000 ml/min. By using these measuring points, a 2nd degree polynomial was laid out with the specified function $y=f(x^2)$ as calibrating function. The correlation coefficient is $R^2=0.9999$.

The illustration of FIG. 2 may be specified as:

$$S_{03}-S_{07}=F_{1,2}(Q_{BK})$$

with:

$F_{1,2}(Q_{BK})$—function of the dialysate flow $Q_{BK}$ between the first pressure measurement location 9 and the second pressure measurement location 13

According to equation (6), the flow resistance R may be measured anytime, i.e., for example, during a preparation or a treatment use of the blood treatment apparatus 1000, online in the blood treatment apparatus 1000 by shutting off ($Q_{sub}=0$) the substitute pump or keeping it constant and by varying the dialysate flow $Q_{BK}$:

$$R = \frac{S_{03} - S_{07}}{2*Q_{BK}} \tag{7}$$

Due to a first valve 19 which is located upstream from the blood treatment module 300 in the secondary circuit 200, and due to a second valve 21 which is located downstream from the blood treatment module 300 in the secondary circuit 200, a non-linear course is obtained for the flow resistance R. As the substitution flow $Q_{sub}$ is usually small as compared to the dialysate flow $Q_{BK}$, the flow resistance R may be approximately determined by varying $Q_{BK}$ around the operating point as follows:

$$R \cong \frac{\Delta(S_{03} - S_{07})}{2*\Delta Q_{BK}} \tag{8}$$

Figure 3:
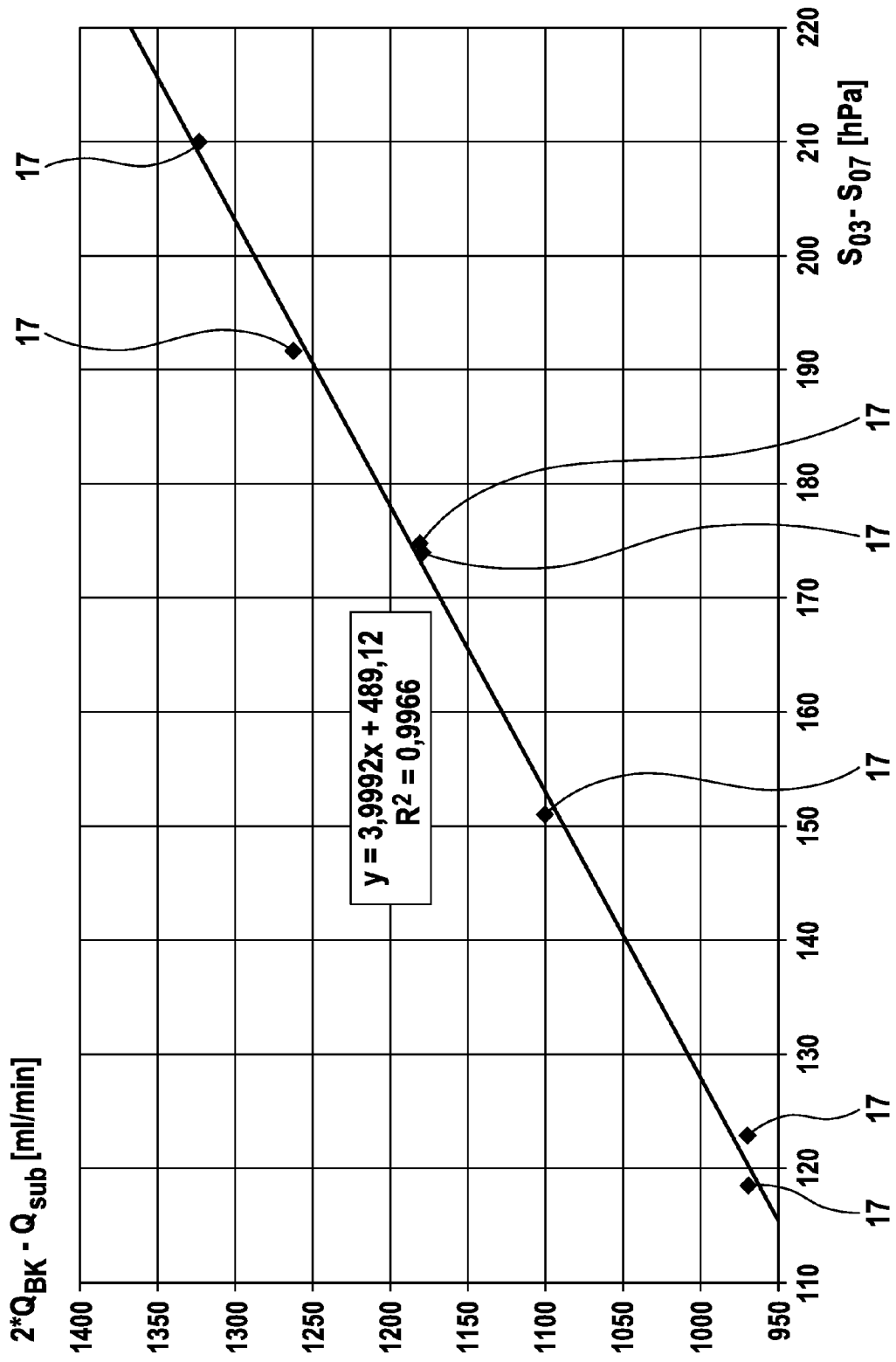
FIG. 3 shows a measured curve of the double second volume flow less a first volume flow over the pressure difference between the first and the second pressure measurement location in the secondary circuit.

FIG. 3 shows a measured curve of the twofold or double dialysate flow $Q_{BK}$ less the substitute flow $Q_{sub}$ depending on the pressure difference between the first pressure measurement location 9 (pressure measurement $S_{03}$) and the second pressure measurement location 13 (pressure measurement $S_{07}$). The dialyzer flow $Q_d$ is constantly 500 ml/min. The blood flow in the primary circuit is $Q_b=450$ ml/min.

In FIG. 3, seven measuring points 17 are spread that were measured with varying substitute flow $Q_{sub}$. The measuring points 17 were recorded with volume flows ($2*Q_{BK}-Q_{sub}$) between 950 ml/min and 1,350 ml/min and pressure difference values ($S_{03}-S_{07}$) between 110 hPa and 220 hPa. By using the measuring points 17, a straight line with the given function $y=f(x)$ is laid out. The correlation coefficient is $R^2=0.9966$.

The gradient of the straight line illustrates the reciprocal flow resistance $1/R$. The substitute flow $Q_{sub}$ may be calculated from this.

The substitute flow $Q_{sub}$ may furthermore also be calculated considering the non-linear flow resistances $R_1$, $R_2$ and considering the ultrafiltrate rate $Q_{uf}$ (shortened: UF rate) which transfers as volume flow in the dialyzer 300 from the primary circuit 100 into the secondary circuit 200.

If in the equation (4a) the products $Q_d*R_1(Q_d)$ or $Q_{BK}*R_2(Q_{BK})$ are replaced by the pressure differences that are illustrated as function of the flows, $$F_{1,m}(Q_d)=Q_d*R_1(Q_d) \tag{9a}$$

$$F_{m,2}(Q_{BK}+Q_{UF})=Q_{BK}*R_2(Q_{BK}) \tag{9b}$$

the following is obtained in general:

$$S_{03}-S_{07}=F_{1,m}(Q_d)+F_{m,2}(Q_{BK}+Q_{UF}) \tag{10}$$

With the aid of the conversion $$S_{03}-S_{07}=F_{1,m}(Q_{BK}+Q_{UF})+F_{m,2}(Q_{BK}+Q_{UF})-(F_{1,m}(Q_{BK}+Q_{UF})-F_{1,m}(Q_d))$$

and the definition $$F_{1,2}(Q_{BK}+Q_{UF})=F_{1,m}(Q_{BK}+Q_{UF})+F_{m,2}(Q_{BK}+Q_{UF})$$

the following is finally obtained:

$$S_{03}-S_{07}=F_{1,2}(Q_{BK}+Q_{UF})-(F_{1,m}(Q_{BK}+Q_{UF})-F_{1,m}(Q_{BK}-Q_{sub})) \tag{11}$$

The function $F_{1,2}$ makes the biggest contribution to the pressure difference $S_{03}-S_{07}$. With the substitution pump being shut off or $Q_{sub}=0$, and with the UF rate $Q_{uf}=0$, $F_{1,2}(Q)$ may be determined online by varying the balancing chamber flow $Q_{BK}=Q$:

$$F_{1,2}(Q)=S_{03}-S_{07} \tag{12}$$

The function $F_{1,m}(Q)$ may be determined device-specifically in the context of type-testing for all devices or by using a factory calibration. Alternatively, the function $F_{1,m}(Q)$ may be set depending on the function $F_{1,2}(Q)$, e.g.:

$$F_{1,m}(Q)=0{,}5*F_{1,2}(Q)+k*Q$$

wherein the term $k*Q$ considers the pressure drop at the dialysate filter 15 (because of the asymmetry of the two distances), or, in general:

$$F_{1,m}(Q)=a*F_{1,2}(Q)+k*Q$$

Normally, the dialysate flow $Q_{BK}$ is significantly higher than the substitute flow $Q_{sub}$ in HDF treatments. The difference $F_{1,m}(Q_{BK}+Q_{UF})-F_{1,m}(Q^d)$ may approximately be replaced by the total differential $dF_{1,m}$. Then, the following is obtained:

$$S_{03} - S_{07} \approx F_{1,2}(Q_{BK} + Q_{UF}) - \left(\frac{dF_{1,m}}{dQ}\right)_{(Q_{BK}+Q_{UF}+Q_d)/2} *Q_{sub} \tag{13}$$

with:
$F_{1,m}$—pressure drop as a function of the volume flow between the first pressure measurement location 9 and the middle of the blood treatment module 300; and
Q—flow rate with the value $(Q_{BK}+Q_{UF}+Q_d)/2$
As the two functions $F_{1,m}(Q)$ and $F_{1,2}(Q)$ are known, the substitute rate $Q_{sub}$ may be calculated from equation (11) or from equation (13).

Figure 4:
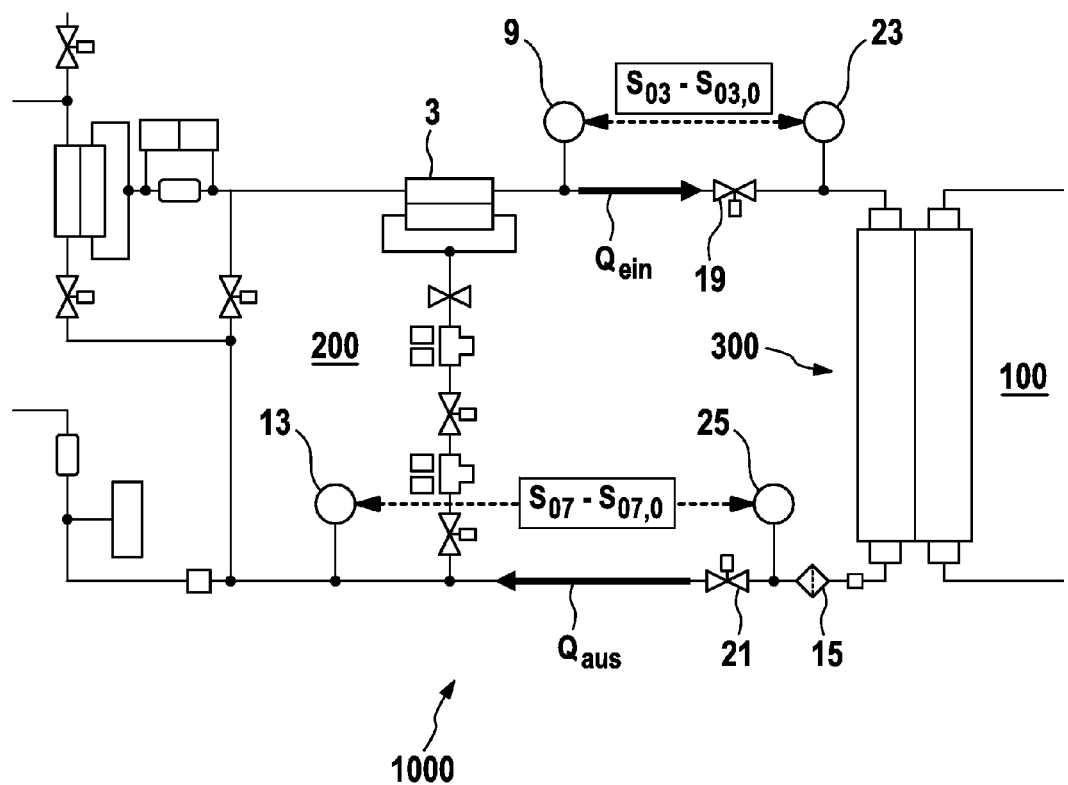
FIG. 4 schematically shows the detail of the secondary circuit of FIG. 1 of the blood treatment apparatus according to a first embodiment of the present invention with two additional pressure measurement locations.

FIG. 4 is based on the illustration of FIG. 1 and shows a blood treatment apparatus 1000 according to the present invention of a second embodiment.

Differing from the blood treatment apparatus illustrated in FIG. 1, the blood treatment apparatus 1000 illustrated in FIG. 4 additionally comprises a third pressure sensor 23 as a third pressure measurement location for recording a third pressure measurement $S_{03,0}$ and a fourth pressure sensor 25 as a fourth pressure measurement location for recording a fourth pressure measurement $S_{07,0}$.

The substitute flow $Q_{sub}$ is introduced into the primary circuit also in this second embodiment—as is shown in FIG. 1—even though this is not separately illustrated in FIG. 4 for clarity reasons.

By using the two additional pressure sensors, i.e., the third pressure sensor 23 and the fourth pressure sensor 25, a dialyzer input flow $Q_{ein}$—by using the pressure difference $S_{03}$–$S_{03,O}$—and a dialyzer output flow $Q_{aus}$—by using the pressure difference $S_{07}$–$S_{07,O}$—may be determined at defined flow resistances. In the present example, the known flow resistances are realized by using the present valves 19 and 21 in the secondary circuit 200. Alternatively, also the use of suited throttles, especially those that work without mechanically moving parts, and the pressure drops of which are within an easily measurable range, instead of valves is provided according to the present invention for determining the flow resistances as described here.

In principle, the difference flow between the flow that flows towards the dialyzer 300 on the input side and the flow that leaves the dialyzer 300 again on the output side, may be determined with this arrangement.

Besides the substitute flow $Q_{sub}$ (not shown in FIG. 4), also the UF rate $Q_{UF}$ (see the description of FIG. 3) as well as a leakage rate $Q_{Leck}$ are recorded with an erroneous balance. The sum of the flows is denoted as a transmembrane flow $Q_{tm}$ which flows over the dialyzer membrane or is exchanged between the primary circuit 100 and the secondary circuit 200 in the dialyzer:

$$Q_{tm} = Q_{sub} + Q_{UF} + Q_{Leck} \quad (14)$$

with:
$Q_{tm}$—transmembrane flow
$Q_{sub}$—substitute flow
$Q_{uf}$—ultrafiltration rate
$Q_{Leck}$—leakage rate If the dialysate flow $Q_{BK}$ in equation (5) is replaced by the sum $Q_d + Q_{sub} + Q_{UF} + Q_{Leck}$, the following is obtained:

$$S_{03} - S_{07} = Q_d * R_1 + (Q_d + Q_{sub} + Q_{UF} + Q_{Leck}) * R_2$$

Thus, the leakage rate $Q_{Leck}$ results to:

$$Q_{Leck} = \frac{S_{03} - S_{07}}{R_2} - Q_d * \left(1 + \frac{R_1}{R_2}\right) - Q_{sub} - Q_{UF} \quad (15)$$

From the gradient of the straight line in FIG. 3, the reciprocal resistance 1/R in the present example results in:

$1/R = 4.0$ ml/min/hPa = 320 ml/h/mmHg.

This value is in the range of the maximum ultrafiltration coefficient (UFK) of dialyzers with a $UFK_{max} = 200$ ml/h/mmHg.

The flow resistances $R_1$ and $R_2$ may be constants. However, they do not have to be constants; in fact, they may vary themselves, e.g., depending on the flow Q.

The tightness of the balancing circle may be tested by using a pressurizing test (DHT). The previously registered leakage rate $Q_{Leck,0}$ may be interpreted as offset and deducted after the DHT:

$$Q_{Leck,eff} = Q_{Leck} - Q_{Leck,0} \quad (16)$$

$$= \frac{(S_{03} - S_{07}) - (S_{03} - S_{07})_0}{R_2} -$$

$$(Q_{sub} - Q_{sub,0}) - (Q_{UF} - Q_{UF,0})$$

What is claimed is:

1. A system for determining at least one volume flow in a blood treatment apparatus, said system comprising:
   a primary circuit configured to conduct a blood to be treated;
   a secondary circuit configured to conduct a fluid that is used for a blood treatment of the blood to be treated;
   a blood treatment module provided as a section of at least one of the primary circuit or the secondary circuit, said blood treatment module configured to at least one of exchange fluids or substances between the primary circuit and the secondary circuit;
   at least one measuring device; and
   a calculating device configured to determine a first volume flow of the secondary circuit as a function of a flow resistance, a second volume flow, and a difference between a second pressure value and a first pressure value, wherein a tube line or connecting line is provided between the primary circuit and the secondary circuit, said tube line or connecting line configured to remove the first volume flow from the second volume flow in the secondary circuit, and introduce said first volume flow into the primary circuit, wherein the first volume flow is a partial volume flow of the second volume flow and wherein the at least one measuring device is configured to measure the first pressure value at a first measurement location in the secondary circuit and the second pressure value at a second measurement location in the secondary circuit.

2. The system for determining at least one volume flow in a blood treatment apparatus according to claim 1, wherein said first pressure measurement location is located upstream from the blood treatment module and downstream from a branch-off of the first volume flow from the second volume flow.

3. The system for determining at least one volume flow in a blood treatment apparatus according to claim 2, wherein said second pressure measurement location is located downstream from the blood treatment module.

4. The system for determining at least one volume flow in a blood treatment apparatus according to claim 3, wherein the system further comprises:
   a device configured to determine the first volume flow as a function of the flow resistance between the first pressure measurement location and the second pressure measurement location.

5. The system for determining at least one volume flow in a blood treatment apparatus according to claim 4, wherein the system further comprises:
   a device configured to determine the flow resistance between the first pressure measurement location and the second pressure measurement location as a function of the second volume flow and the difference between the second pressure value and the first pressure value.

6. The system for determining at least one volume flow in a blood treatment apparatus according to claim 5, wherein the flow resistance is determined by the device using a function which is linearized in an area of an operating point of the second volume flow and of the difference between the second pressure value and the first pressure value.

7. The system for determining at least one volume flow in a blood treatment apparatus according to claim 4, wherein the blood treatment apparatus is configured to perform hemodialysis or hemodiafiltration.

8. The system for determining at least one volume flow in a blood treatment apparatus according to claim 1, the system further comprising:
    at least one of two pressure measurement locations that are located in or at the secondary circuit upstream from the blood treatment module or two pressure measurement locations that are located in or at the secondary circuit downstream from the blood treatment module.

9. The system for determining at least one volume flow in a blood treatment apparatus according to claim 1, wherein the calculating device is further configured to determine a volume flow of the secondary circuit upstream from the blood treatment module as a function of a first pressure difference by a pressure difference determination at defined flow resistances.

10. The system for determining at least one volume flow in a blood treatment apparatus according to claim 1, wherein the calculating device is further configured to determine a volume flow of the secondary circuit downstream from the blood treatment module as a function of a second pressure difference by a pressure difference determination at defined flow resistances.

* * * * *